United States Patent
Dittmann et al.

[11] Patent Number: 5,858,241
[45] Date of Patent: Jan. 12, 1999

[54] COLUMN FOR CAPILLARY CHROMATOGRAPHIC SEPARATIONS AND METHOD OF MANUFACTURING SAME

[75] Inventors: Monika Dittmann, Marxzell; Gerard Rozing, Karlsruhe; Klaus K. Unger, Seeheim; Thomas Adam, Saarlouis, all of Germany

[73] Assignee: Hewlett-Packard Company, Palo Alto, Calif.

[21] Appl. No.: 856,659

[22] Filed: May 15, 1997

[30] Foreign Application Priority Data

May 20, 1996 [EP] European Pat. Off. .............. 96107979

[51] Int. Cl.⁶ .................................................. B01D 15/08
[52] U.S. Cl. ........................................ 210/656; 210/198.2
[58] Field of Search .................................... 210/635, 656, 210/198.2, 502.1; 141/12, 80

[56] References Cited

U.S. PATENT DOCUMENTS

| | | | |
|---|---|---|---|
| H896 | 3/1991 | Szakasits | 210/198.2 |
| 3,005,514 | 10/1961 | Cole et al. | 183/2 |
| 3,295,296 | 1/1967 | Halasz | 210/198.2 |
| 3,808,125 | 4/1974 | Good | 210/31 C |
| 4,211,658 | 7/1980 | McDonald et al. | 210/198.2 |
| 4,217,027 | 8/1980 | MacChesney et al. | 350/96.3 |
| 4,293,415 | 10/1981 | Bente, III et al. | 210/198.2 |
| 4,563,276 | 1/1986 | Clark et al. | 210/198.2 |

FOREIGN PATENT DOCUMENTS

| | | | |
|---|---|---|---|
| 427 351 | 6/1907 | Switzerland | 210/656 |
| 1123044 | 8/1965 | United Kingdom | 210/198.2 |

OTHER PUBLICATIONS

European Search Report, EP 96 10 7979, dtd 18. 10. 96.
Chromatagraphia, vol. 38, No. 9/10, p. 649 ff., (1994) The Analysis of Pharmaceutical Compounds Using Electrochromatography, Smith et al.
Chromatagraphia, vol. 408, No. 5/60, p. 329 ff., Capillary Electrochromatography . . . , Boughtflower et al. (1995).
Analytical Chemistry, vol. 53, No. 8, Jul. '81, p1298 ff., Zone Electroophoresis in Open tubular Glass Capillaries, Jorgenson et al.
Theory and Practice of Capillary Electrochromatography, Hewlett–Packard Publication 12–5964–5930E, pp. 1–11.
Rozin, LC–GC Magazine vol. 13, No. 10, pp. 800–814, Oct. 1995.

*Primary Examiner*—Ernest G. Therkorn

[57] ABSTRACT

A column for capillary chromatographic separations, for example high performance liquid chromatography, capillary electrochromatography, or supercritical chromatography, comprises a column bed of packing material arranged in the inner bore of a capillary, wherein said bed of packing material is completely immobilized by a thermal treatment. The thermal treatment preferably comprises moving a heating wire along the column while applying pressure to the column using a high pressure pump.

3 Claims, 3 Drawing Sheets

CHROMATOGRAMS OF A STANDARD SAMPLE BEFORE AND AFTER IMMOBILIZATION OF PACKET BED.
1 THIOUREA, 2 METHYLPARABENE, 3 ETHYLPARABENE, 4 PROPYLPARABENE, 5 BUTYLPARABENE, 6 NAPHTHALENE, 7 FLUORENE, 8 PHENANTHRENE, 9 ANTHRACENE, 10 FLUORANTHENE

COLUMN FOR CAPILLARY CHROMATOGRAPHIC SEPARATIONS AND METHOD OF MANUFACTURING SAME

FIELD OF THE INVENTION

The invention relates to a column for capillary chromatographic separations, for example for high performance liquid chromatography, or capillary electrochromatography, or supercritical chromatography. The invention also relates to a method for manufacturing such a column.

BACKGROUND OF THE INVENTION

Capillary chromatographic separation methods are preferably performed in fused silica (FS) tubing with internal diameters ranging from 5–530 µm. Such tubing consists of a silica (SiO2) glass drawn at high temperature (1300° C.) from a quartz preform provided with a protective outside layer from polyimide or aluminum. Robustness, tensile strength, high pressure resistance and bend stability are favorable mechanical properties of FS tubing. High chemical purity and well defined surface of the tubing provides in most cases low interaction with solutes and leads to optimum separation in many applications.

In U.S. Pat. No. 4,293,415 Dandeneau et al. describe the usage of a fused silica capillary, which may have wall coatings on the inside surface to stimulate specific interactions and/or further minimize secondary undesired solute/surface interactions, for open tubular capillary gas chromatography (CGC) and open tubular supercritical fluid chromatography (SFC). Jorgenson et al. (Anal. Chemistry, 1981, 53, p. 1298) have demonstrated that such capillaries are also ideally suited for the newer technique of capillary electrophoresis (CE).

It has been demonstrated that FS tubing can also be used for capillary separations performed in a packed bed, such as SFC, µ-HPLC and capillary electrochromatography (CEC). The mechanical properties of fused silica capillaries suffice to withstand the high pressure that occurs either when packing the tubing with small particles using a high pressure filtration technique or when operating the column especially in HPLC mode.

In FS (or other small i.d.) tubing the packing material in the column bed needs to be retained in the tubing; otherwise hydraulic or electrical forces drive the particles out of the capillary column. This is in most cases achieved by porous frits that are formed in the capillary by different processes.

In recent publications frits have been formed from the stationary phase particles directly by application of heat to a zone of the packed fused silica column where the terminating frit needs to be (e.g. Boughtflower et al., Chromatographia 40, 329 (1995), Smith et al., Chromatographia 38, 649 (1994), Rozing et al., LC-GC Magazine, October 1995). It is believed that under these conditions the particles are glued together by the fact that upon heating a small amount of silica dissolves in water forming silicic acid, and that upon cooling the repolymerized silicic acid deposits between the particles. The advantage of this approach is that it does not substantially alter the chemical constitution of the zone that is fritted, that it can be done on the inlet and outlet side without problem, that the length of the fritted zone is well controlled by the dimension of the external heating source used and that the porosity of the bed is unaffected. Photographs e.g. by Boughtflower et al., show that the particle structure is not affected by this treatment and therefore inter-particle porosity is maintained.

The main problem with all these approaches is that although the packing is in principle retained between the frits, the stationary phase particles still have the ability to move or rearrange within the boundaries determined by the frits. It has been observed that the stationary phase particles in packed capillaries rearrange during standard operation of such a capillary, resulting in formation of voids (unpacked stretches) between the retaining frits. The reason for this are the electric and/or hydraulic forces that act upon the particles during column operation, which lead to changes in packing density. These voids lead to chromatographic artifacts like loss of efficiency, tailing peaks etc.

SUMMARY OF THE INVENTION

It is thus an object of the present invention to provide a packed column for capillary chromatography and a corresponding manufacturing method, wherein the packing material is immobilized over the whole length of the column.

In particular, it is an object of the invention to avoid or reduce the above mentioned problems associated with rearrangement of particles in the packing and subsequent formation of voids or unpacked stretches.

A column according to the invention for capillary chromatographic separations, for example high performance liquid chromatography, capillary electrochromatography, or supercritical chromatography, comprises a column bed of packing material arranged in the inner bore of the column wherein the packed bed is completely immobilized by a thermal treatment described below.

According to a preferred embodiment of the present invention, the mentioned prior art problems are circumvented in the following way. The fused silica tubing that is used for preparation of a micro high performance liquid chromatography or CEC is packed in the usual way (see e.g. Boughtflower et al., Rozing et al.). After the column packing is finished, instead of preparing the retaining frits, the complete packing bed is immobilized by a thermal treatment. This is done the following way: A coiled heating wire with the capillary to be treated in the center of the coil is slowly moved along the column. During this process pressure is applied to the inlet side of the column to generate a flow through the packed bed. Under these conditions the immobilization takes place due to the following mechanism. At the elevated temperatures induced by the heating coil a small amount of silica is dissolved to form silicic acid. The silicic acid molecules are then transported by the hydraulic flow to a colder region of the packing where they repolymerize and deposit between the stationary phase particles acting as a glue.

DETAILED DESCRIPTION OF THE PREFERRED EMBODIMENTS

Figure 1:
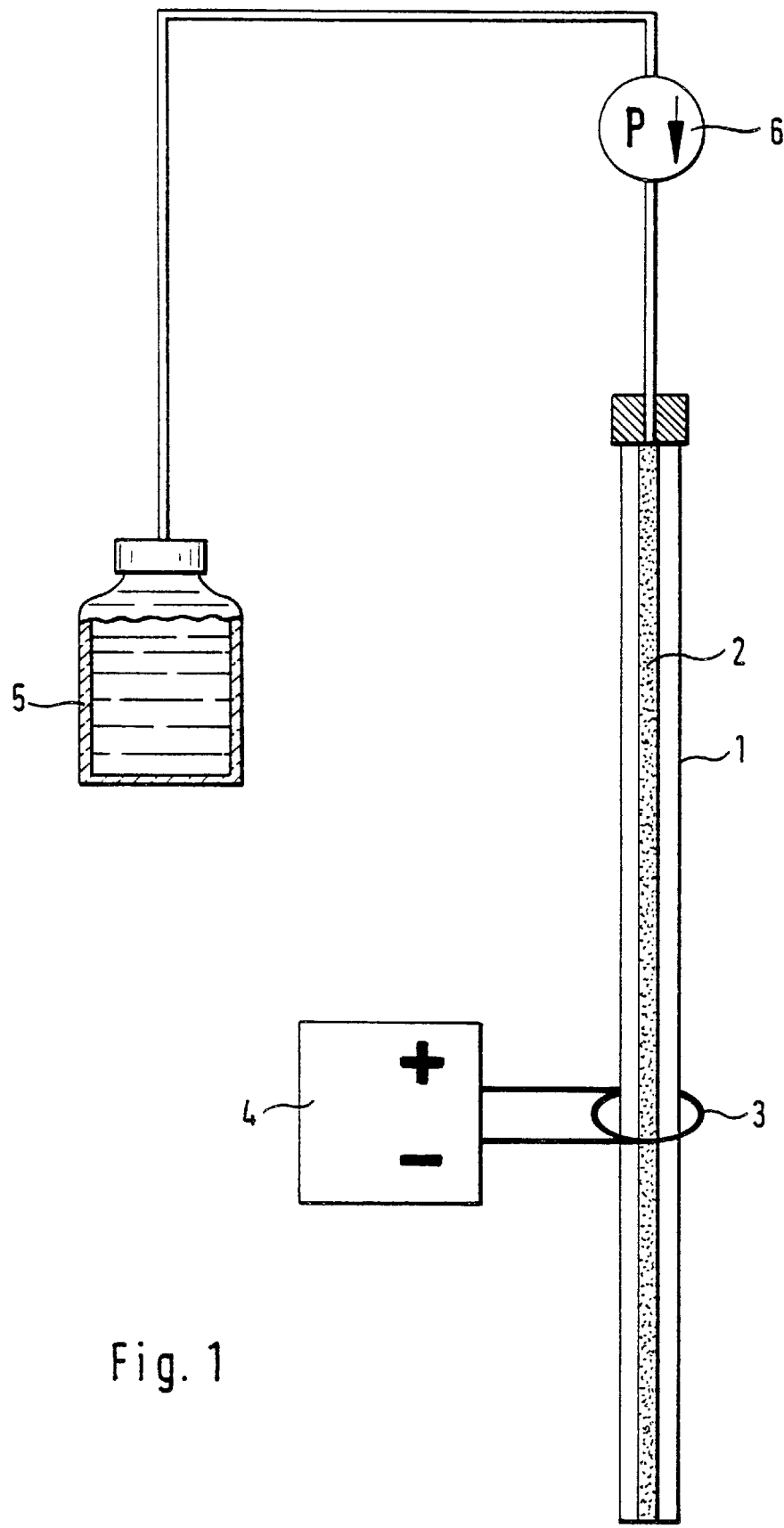
FIG. 1 is a schematic diagram of an embodiment of the invention.

FIG. 1 shows a packed column 1 according to a first embodiment of the invention. The column is made of fused silica and typically has a length of about 5–200 cm. The column has an interior diameter in the range between about 5–530 micrometers. The interior of the column is filled over the major part of its length with a packed bed 2 which serves for separating the sample substances passing through the column. The immobilization of the packing bed is achieved by moving the heating coil 3 which is connected to a power supply 4 along the column 1 with an appropriate speed. During this process a liquid 5 (preferably water) is pumped through the column using a high pressure pump 6. The velocity with which the heating coil is moved along the column and the liquid flow rate through the packing bed depend on the nature of the packing material to be immobilized and have to be determined experimentally. A typical velocity for the heating coil would be 2 mm/s and a typical liquid flow velocity would be 1–2 mm/s. The temperature of the heating coil is chosen such that the temperature inside the capillary is about 300°–400° C. In the process described the polyimide coating on the outside of the capillary is not removed or destroyed. This is important to retain the mechanical strength of the capillary.

Figure 2:
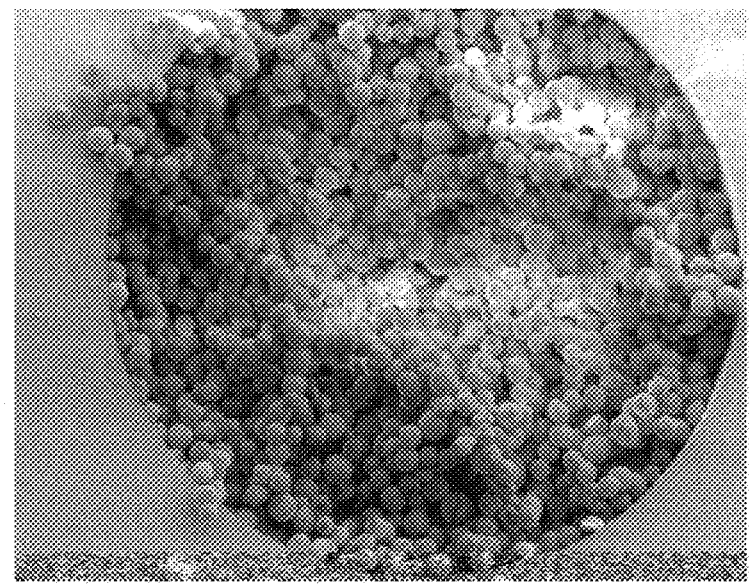
FIG. 2 shows an electromicroscopic picture of the immobilized zone of a column of the invention.

FIG. 2 shows an electromicroscopic picture of the immobilized zone demonstrating that the structure of the packing particles is unaltered and that the permeability of the packed bed is unchanged. This factor is important for the chromatographic performance of the column. Chromatographic experiments have shown that the retention properties of the stationary phase are not altered by the immobilization process.

Figure 3:
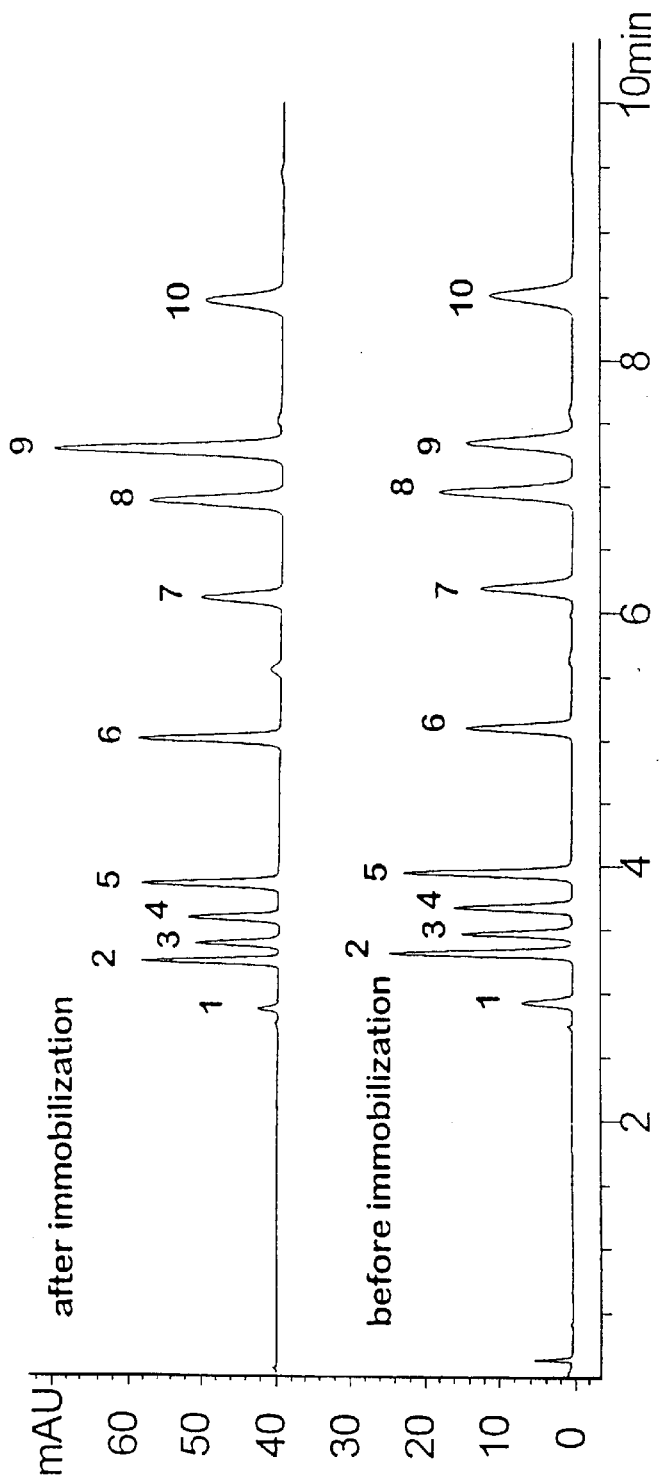
FIG. 3 is a comparison of chromatograms on a packed capillary before and after immobilization.

FIG. 3 shows chromatograms of a standard sample on a packed capillary before (a) and after (b) immobilization.

According to the invention it is thus possible to generate an immobilized packed bed in which the packing particles are "glued" together without altering the mechanical, chemical and chromatographic properties of the packing. This results in better long term stability of the chromatographic bed.

We claim:

1. A method of manufacturing a column for capillary chromatographic separations, comprising the steps of:

filling stationary phase packing material into and along a determined length of a capillary;

immobilizing all of the stationary phase packing material inside the capillary by application thereto of a thermal treatment along an entirety of said determined length; and applying pressure to an inlet side of the capillary during the thermal treatment to enable a flow of a portion of said stationary phase packing material to a colder region of said capillary where said portion solidifies and acts to bind said stationary phase packing material.

2. The method as recited in claim 1, wherein the thermal treatment comprises the step of:

moving a heating coil along the entirety of said determined length of said column that is filled with said stationary phase packing material.

3. The method as recited in claim 1, wherein:

the heating coil is an electrical heating coil having a center axis, with the capillary being arranged along the center axis of the electrical heating coil, the pressure is applied in the form of an hydraulic flow, the heating coil is moved at velocities of 0.5–5 mm/s opposite to a direction of the applied hydraulic flow which in turn moves at 0.5–5 mm/s under a linear pressure gradient over stationary phase packing material, ranging from 100–1000 bar to atmospheric pressure.

* * * * *